United States Patent [19]
Quick et al.

[11] Patent Number: 5,665,051
[45] Date of Patent: Sep. 9, 1997

[54] ENDOSCOPE WITH AXIALLY MOVABLE OPTICAL FIBER GUIDE TO COMPENSATE CHANGES IN LENGTH

[75] Inventors: Richard L. Quick, Trabuco Canyon; John F. Forkner, South Laguna; Gary M. Woker, Escondido, all of Calif.

[73] Assignee: Imagyn Medical, Laguna Niguel, Calif.

[21] Appl. No.: 289,932

[22] Filed: Aug. 12, 1994

[51] Int. Cl.[6] ............................................. A61B 1/00
[52] U.S. Cl. ........................ 600/161; 600/182; 600/163
[58] Field of Search ........................... 600/182, 133, 600/161, 167, 168, 163, 162; 385/90, 119, 116, 117

[56] References Cited

U.S. PATENT DOCUMENTS

| | | | |
|---|---|---|---|
| 2,026,176 | 12/1935 | Jaeckel | 600/168 |
| 2,975,785 | 3/1961 | Sheldon | 600/161 |
| 4,063,796 | 12/1977 | Hiltebrandt | 600/161 |
| 4,501,477 | 2/1985 | Sunaga | 385/117 |
| 4,650,279 | 3/1987 | Magee . | |
| 4,704,007 | 11/1987 | Landre et al. | 600/167 |
| 4,776,668 | 10/1988 | Fujimoto | 385/117 |
| 4,813,400 | 3/1989 | Washizuka et al. | 600/182 |
| 4,899,732 | 2/1990 | Cohen | 600/182 |
| 5,199,417 | 4/1993 | Muller et al. | 600/163 |
| 5,279,280 | 1/1994 | Bacich et al. . | |
| 5,304,171 | 4/1994 | Gregory et al. | 606/7 X |
| 5,443,057 | 8/1995 | Elmore | 600/182 |

FOREIGN PATENT DOCUMENTS

| | | | |
|---|---|---|---|
| 122713 | 10/1984 | European Pat. Off. | 385/119 |
| 2245718 | 1/1992 | United Kingdom | 385/119 |

*Primary Examiner*—Richard J. Apley
*Assistant Examiner*—John P. Leubecker
*Attorney, Agent, or Firm*—Donald E. Stout

[57] ABSTRACT

A fiberoptic endoscope includes an axially movable optical fiber guide to compensate for focusing effects, such as thermal expansion or mechanical tolerances. The distal end portion of the optical fiber guide is secured to the distal end of the endoscope while the proximal end portion is permitted to move axially relative to a proximal housing portion of the endoscope. The proximal housing portion includes an eye lens unit secured thereto. A decoupling lens unit is fixed to the proximal end portion of the optical fiber guide so as to move therewith with respect to the eye lens unit.

30 Claims, 4 Drawing Sheets

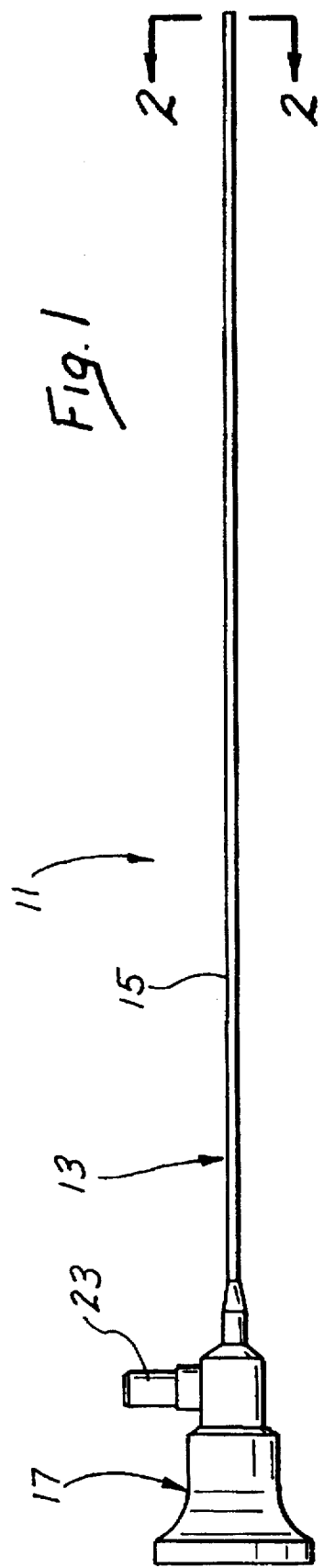
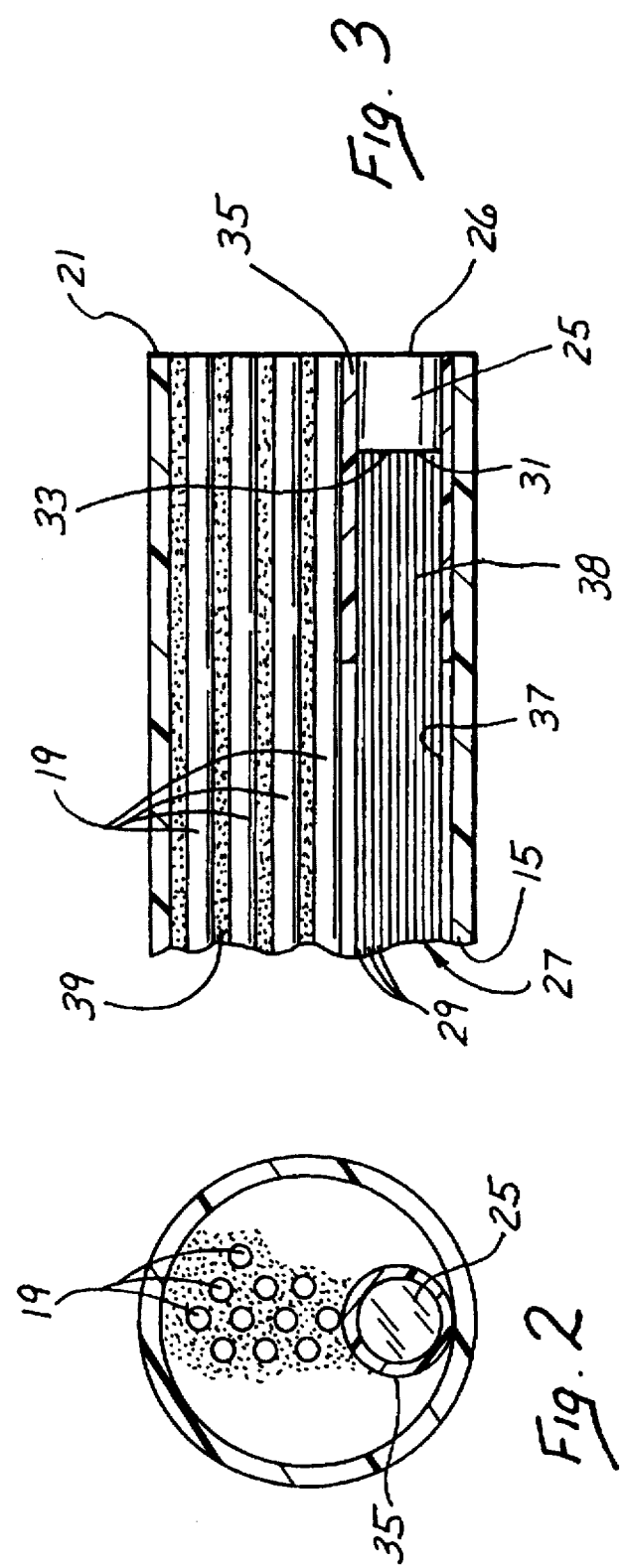

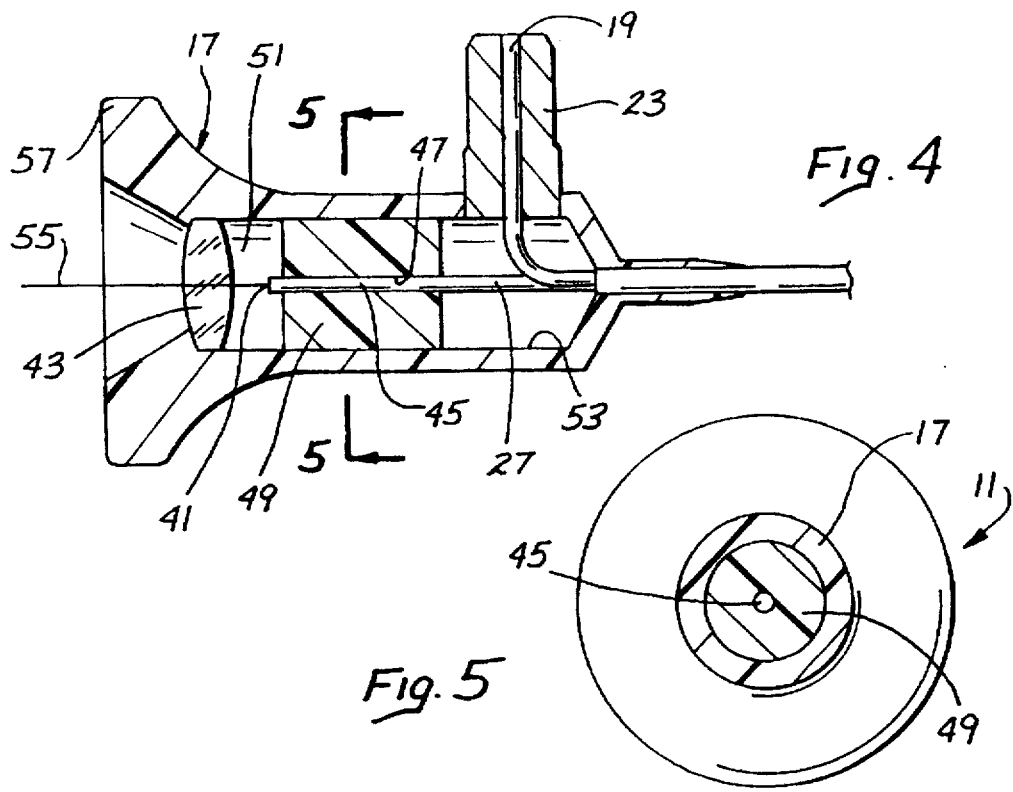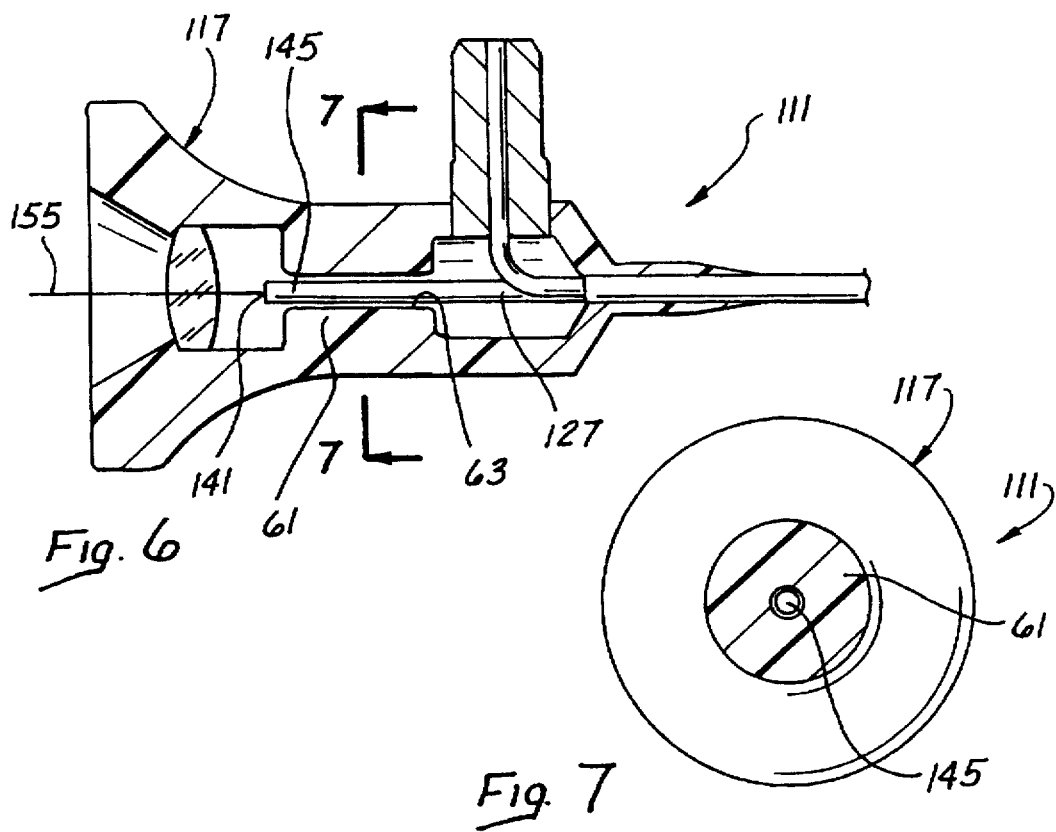

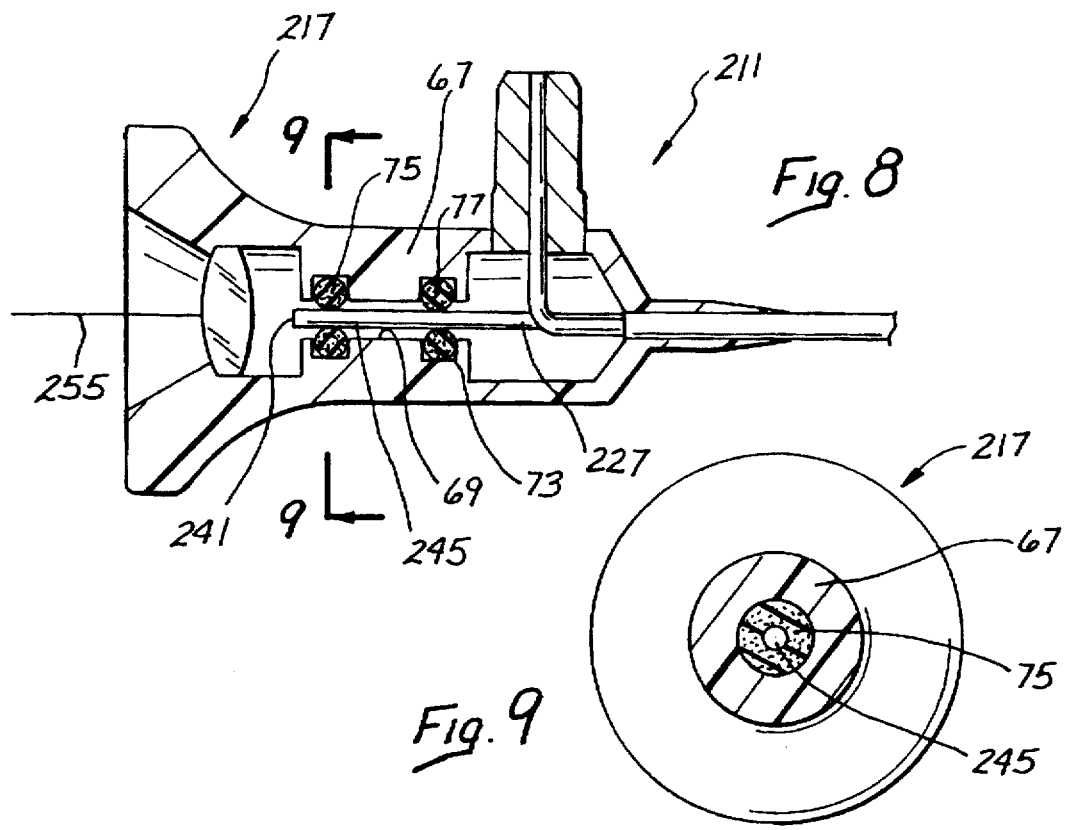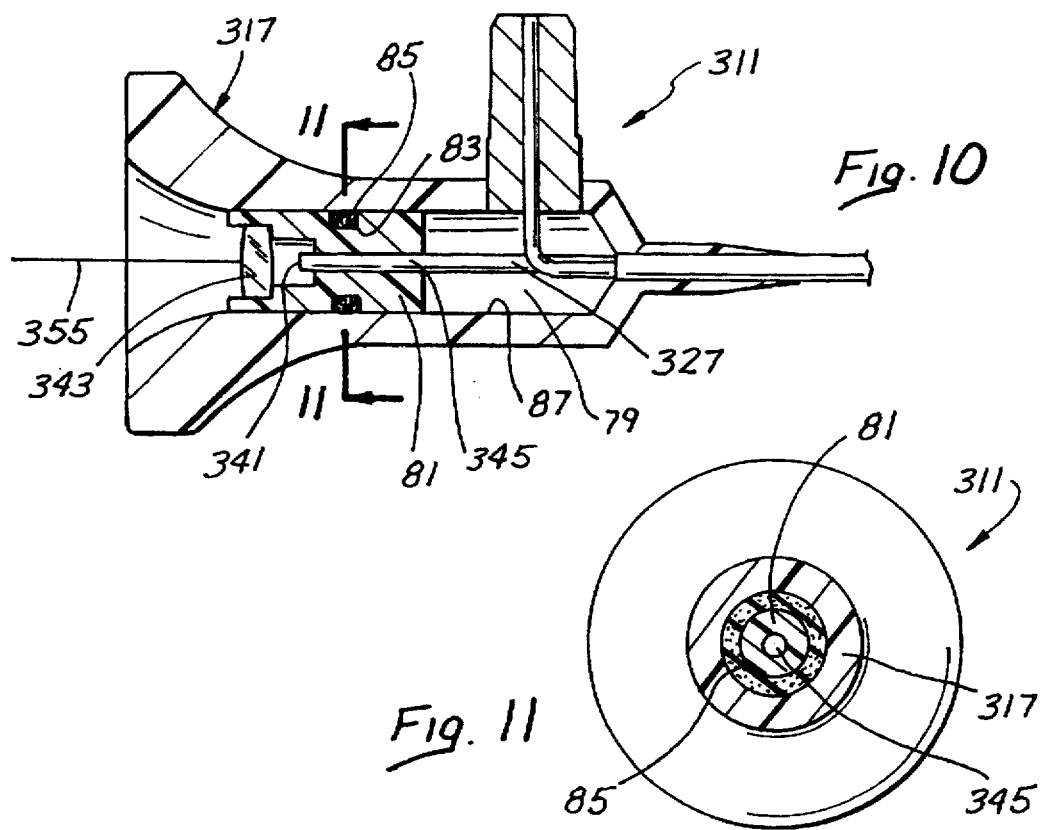

ENDOSCOPE WITH AXIALLY MOVABLE OPTICAL FIBER GUIDE TO COMPENSATE CHANGES IN LENGTH

BACKGROUND OF THE INVENTION

Endoscopes are commonly used to view the interior passage of an object. Endoscopes have industrial applications wherein the endoscope is used to view a passage within, for example, a piece of equipment. Endoscopes also have medical applications wherein the endoscope is used to view a passage within the body of a patient.

An endoscope typically includes an endoscope body and optical components carried by the endoscope body to enable viewing of the passage distally of the distal end of the endoscope body. The optical components may include illumination optics for illuminating the field of view, and such illumination optics may comprise optical fibers carried by the endoscope body.

The optical components also include the optics necessary to transmit or relay an image proximally and to provide the image to an eyepiece for direct visualization or to a camera which enables viewing of the scene on a TV monitor. These latter optics may include an elongated fiberoptic image guide, comprising a fiberoptic imaging bundle having a plurality of fibers for transmitting the image proximally, a distal objective lens system located adjacent to the distal end of the fiberoptic image guide, and an ocular lens assembly adjacent the proximal end of the endoscope body.

A characteristic of endoscopes of this type is that the fibers in such devices typically have a relatively high (0.30 to 0.50) numerical aperture in order to capture as much light as possible from the subject. Additionally, the ocular lens assembly typically comprises an eyepiece lens having a high magnification power. The high numerical aperture together with the small diameter of the fibers and the high magnification power of the eyepiece lens tends to result in a very shallow depth of focus at the eyepiece. In other words, very small linear shifts of the proximal end of the image guide with respect to the eyepiece lens can cause the image to quickly become out of focus because of the shallow depth of focus of the eyepiece lens. This is critical when focusing effects are present which tend to cause the distance between the eyepiece lens and the proximal end of the image guide to vary. Such focusing effects may include thermal expansion of the length of the fiber optic bundle or mechanical tolerances on the placement of the ocular lens assembly elements, for example.

Another aspect involves subjecting the endoscope or components thereof to varying temperatures. For example, endoscopes for medical use are typically reusable. Between uses it is desirable to sterilize the endoscope, for example, at elevated temperatures. Since the endoscope is typically constructed from materials having varying coefficients of thermal expansion, prolonged exposure to heat can damage the mechanical as well as the optical integrity of the endoscope. In addition, in other (non-medical) use applications, endoscopes may be subjected to varying temperatures, such as use at quite elevated temperatures followed by storage at room temperature, or use at two or more different temperatures. Because of such temperature differences, mechanical and/or optical damage to the scope can result.

One type of fiberoptic image guide utilizes at least partially non-fused image fibers which, because of its inherent flexibility, can accommodate any longitudinal translation. However, from a cost and manufacturing standpoint, fiberoptic image guides made from at least partially non-fused fibers are not practical. Due to their inherent fragility, the manufacturing costs are high and they are typically characterized by low resolution.

Alternately, scopes which utilize entirely fused fiberoptic image guides may be made from 1,000 to 60,000 individual fibers and are particularly useful in small sizes which cannot be sufficiently managed by classical glass lens technology. These image guides can be incorporated into flexible or rigid endoscope systems. To consistently maintain optical and mechanical integrity, these image guides are typically bonded at both ends, proximal and distal, to the endoscope body or sheath. A distal lens assembly, which is fixed to the endoscope body, is located distally of the image guide. The proximal portion of the fiberoptic image guide is fixed to the endoscope body so that a repeatable connection to a camera coupling or eyepiece can be made. One limitation of this type of endoscope system is that during temperature change the fiberoptic bundle may expand at a different rate relative to the body or sheath to which it is bonded and, in so doing, cause mechanical and/or optical damage to the endoscope.

One method which has been suggested to accommodate the expansion properties of a fused fiberoptic image guide and endoscope body is to build into the design an area for relaxation in the image guide to take place. However, curved portions of an image guide are not always possible or practical. Larger diameter guides are inherently less flexible or readily curvable within the endoscope body or sheath. From a practical standpoint, medical endoscopes are purposely designed to use a minimal amount of space to allow for easier access to smaller areas of the body and smaller insertion modalities. Providing an endoscope design with sufficient area for accommodating a curved image guide would not be space efficient.

Therefore, it would be advantageous to provide an endoscope which can be subjected to prolonged exposure at varying temperatures, for example, during sterilization or use, without damaging the mechanical and/or optical integrity of the endoscope.

It would additionally be advantageous to provide an endoscope which is capable of a much larger tolerance for focusing effects such as thermal expansion of the length of the fiber optic bundle or mechanical tolerances on the placement of the ocular lens elements, without focus adjustment. This would, for example, permit the interchange of fiberoptic bundles on a fixed-focus eyepiece without excessively tight mechanical tolerances.

SUMMARY OF INVENTION

The invention solves the problems described above by providing a new endoscope which can be exposed to environments of varying temperature without being damaged. This results in substantial benefits which are achieved in a space efficient and cost effective manner.

Also provided by the invention is a new endoscope which has a large tolerance for focusing effects, thereby permitting easy and convenient use of the endoscope in all environments, even one having significant focusing effects, such as thermal expansion of the length of the fiberoptic bundle or mechanical tolerances on the placement of the eyepiece lens elements, without the need to frequently refocus the image. Even more importantly, the larger tolerance for focusing effects permits the use of a fixed focus eyepiece, which saves considerable cost and complexity, and further allows for the interchanging of fiberoptic bundles on a fixed-focus endoscope without excessively tight mechanical tolerances.

In one broad aspect, the present invention is directed to endoscopes which comprise an endoscope body that is elongated and has r distal end, and a fiberoptic image guide, preferably a fused fiberoptic image guide, that is elongated and is located in the endoscope body. This fiberoptic image guide is effective for transmitting an image proximally. The fiberoptic image guide includes a distal end portion which is secured to the endoscope body and a proximal end portion which is not secured to the endoscope body. The proximal end portion of the fiberoptic image guide is preferably free to move axially relative to the endoscope body. Although one or both of the endoscope body and fiberoptic image guide may be flexible, it is preferred that both these elements be substantially rigid. Thus, allowing the proximal end portion of the fiberoptic image guide to move axially relative to the endoscope body is particularly attractive when both the image guide and the endoscope body are substantially rigid and, therefore, have little or no ability to bend, for example, to accommodate changes in length due to exposure to different temperatures.

The present endoscope structures are very advantageous when the endoscope body, and particularly the endoscope sheath, which extends over a substantial portion of the length of the image guide, has a different coefficient of thermal expansion relative to the fiberoptic image guide. The present invention allows for the use of materials of construction which have different coefficients of thermal expansion and are optimally effective for use in a given endoscope without concern for axial expansion which may result by exposing the endoscope to different temperatures.

In a particularly useful embodiment, the endoscope further comprises a distal lens assembly or objective secured to the endoscope body and located distally of the fiberoptic image guide. This distal lens assembly acts to form an image which is then passed by the image guide proximally. The endoscope preferably includes an ocular lens assembly located proximally of the fiberoptic image guide. This ocular lens assembly passes an image transmitted proximally by the fiberoptic image guide for visualization. In the event that the field of view to be visualized by the endoscope is dark, the endoscope can include illumination optics carried by the endoscope body for transmitting illumination distally of the endoscope body.

In another useful embodiment, the present endoscopes further comprise a positioning assembly located in the endoscope body for substantially maintaining the radial position of the proximal end portion of the fiberoptic image guide relative to the endoscope body as the proximal end portion moves axially relative to the endoscope body. The positioning assembly may be operatively coupled to the endoscope body so as to be substantially stationary in the axial direction relative to the endoscope body. Alternately, the proximal end portion of the fiberoptic image guide is secured to the positioning assembly which is adapted to move axially, with the proximal end portion of the image guide, relative to the endoscope body.

Various configurations of the present positioning assembly may be employed. For example, any structure which is effective to substantially maintain the radial position of the proximal end portion of the fiberoptic image guide relative to the endoscope body as the proximal end portion moves axially relative to the endoscope body may be utilized. Various embodiments of positioning assemblies are as follows.

In one embodiment, the positioning assembly defines an axially extending passage in which the proximal end portion of the fiberoptic image guide is received, and preferably secured. In this embodiment, the positioning assembly is sized and adapted to move axially relative to the endoscope body.

In another embodiment, the positioning assembly includes a circumferential projection extending radially inwardly from the endoscope body and surrounding the proximal end portion of the fiberoptic image guide. In this embodiment, the positioning assembly is restricted against axial movement relative to the endoscope body. The positioning assembly, in particular the circumferential projection, is preferably an integral part of the endoscope body.

In an additional embodiment, the positioning assembly includes at least one resilient annular element, and preferably two resilient annular elements, adapted to receive the proximal end portion of the fiberoptic image guide. Such resilient annular elements, which may comprise O-rings, are preferably operatively coupled to the endoscope body so as to be effectively restricted against axial movement relative to the endoscope body.

In a further embodiment, the positioning assembly carries at least a portion of the ocular lens assembly. In this embodiment, the proximal end portion of the fiberoptic image guide is preferably secured to the positioning assembly which, in turn, is sized and adapted to move axially relative to the endoscope body. The distance between the proximal end of the fiberoptic image guide and that portion of the ocular lens assembly carried by the positioning assembly remains substantially constant, thus reducing optical defocusing which may result from the axial movement of the proximal end portion of the image guide. A seal assembly is preferably provided and is located between the endoscope body and the positioning assembly to effectively prevent the flow of fluid across the seal assembly (i.e. into or out of the interior of the endoscope).

In still another important aspect of the invention, an endoscope is provided which advantageously has a significantly increased focusing tolerance compared to prior art endoscopes. The endoscope has an elongated endoscope body, including a proximal housing portion. An elongated fiberoptic image guide in the endoscope body has a distal end and a proximal end, and is adapted for transmitting an image proximally through the endoscope. The focusing tolerance is improved because the optical magnification power of the eyepiece lens is split between two or more lenses, so that the ocular lens assembly located in the proximal housing portion includes both a decoupling lens unit and an axially spaced eye lens unit, which is preferably fixed to the proximal housing portion. It is preferable that the decoupling lens unit have a high magnifying power and the eye lens unit have a low magnifying power, in order to maximize the increased focusing tolerance. The decoupling lens unit is in a fixed mechanical relationship with the fiberoptic image guide, and preferably in direct fixed optical contact with the proximal end thereof. One especially advantageous way to affix the decoupling lens unit to the fiberoptic image guide is to use an index-matched adhesive system.

In a particularly useful embodiment of the invention, the decoupling lens unit actually comprises a plurality of lenses, preferably including a first lens adjacent to the proximal end of the fiberoptic image guide and a second lens axially spaced from the first lens, between the fast lens and the eye lens unit. Again, it is advantageous for the first lens to be in direct fixed optical contact with the proximal end of the fiberoptic image guide, which contact is preferably achieved using an index-matched adhesive system. In the preferred embodiment, the decoupling lens unit includes a decoupling lens cell, having a base portion which is fixedly attached to the proximal end of the fiberoptic image guide and a peripheral wall portion which extends proximally toward the eye lens unit. The second lens is fixedly attached to the peripheral wall portion and the fast lens is in direct fixed optical contact with the proximal end of the fiberoptic bundle, so that the first and second lenses are in fixed axially spaced relationship to one another. In order to accommodate focusing effects such as thermal expansion or mechanical tolerancing, the decoupling lens cell is sized and adapted to slide axially within a space in the endoscope proximal housing portion, thereby varying the axial distance between the decoupling lens unit and the eye lens unit.

In a further aspect a further aspect of the invention, an endoscope is provided which comprises an elongated endoscope body with a proximal housing portion and an elongated fiberoptic image guide therein, having a distal end and a proximal end and being adapted for transmitting an image proximally through the endoscope. A unique feature of the inventive endoscope is that a lens is located in the proximal housing portion, which has optical magnification power and is in direct fixed optical contact with the proximal end of the fiberoptic image guide. The lens is preferably affixed to the proximal end of the image guide with an index-matched adhesive system.

In still another aspect of the invention, there is provided an endoscope which combines the features of enlarged focusing tolerance with an ability for the proximal end of the fiberoptic image guide to move freely axially with respect to the endoscope body. The inventive endoscope includes an endoscope body which is elongated and has a distal end and a proximal housing portion. An elongated fiberoptic image guide lies in the endoscope body, which is adapted for transmitting an image proximally through the endoscope. The fiberoptic image guide includes a distal end portion which is secured to the endoscope body and a proximal end portion which is not secured to the endoscope body, so that it is free to move axially responsive to thermal expansion or other focusing effects. An ocular lens assembly is located in the proximal housing portion, through which the image is transmitted proximally by the fiberoptic image guide to be visualized by a user or camera. In order to expand the focusing tolerance of the endoscope, as discussed supra, the ocular lens assembly includes both a decoupling lens unit and an axially spaced eye lens unit, wherein the decoupling lens unit is in a fixed mechanical relationship with the fiberoptic image guide.

Although many of the features of the present invention are described separately, more than one or all of such features can be used in various combinations, provided that such features are not mutually inconsistent, and all of such combinations are within the scope of the present invention.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a side elevational view of an endoscope constructed in accordance with the teachings of this invention.

FIG. 2 is an enlarged sectional view taken generally along line 2—2 of FIG. 1.

FIG. 3 is an enlarged, fragmentary, axial sectional view through a distal region of the endoscope.

FIG. 4 is an axial sectional view through a proximal region of the endoscope.

FIG. 5 is a sectional view taken generally along line 5—5 of FIG. 4.

FIG. 6 is an axial sectional view through a proximal region of a first alternate endoscope constructed in accordance with the teachings of the present invention.

FIG. 7 is a sectional view taken generally along line 7—7 of FIG. 6.

FIG. 8 is an axial sectional view through a proximal region of a second alternate endoscope constructed in accordance with the teachings of the present invention.

FIG. 9 is a sectional view taken generally along line 9—9 of FIG. 8.

FIG. 10 is an axial sectional view through a proximal region of a third alternate endoscope constructed in accordance with the teachings of the present invention.

FIG. 11 is a sectional view taken generally along line 11—11 of FIG. 10.

DETAILED DESCRIPTION OF THE DRAWINGS

Figure 12:
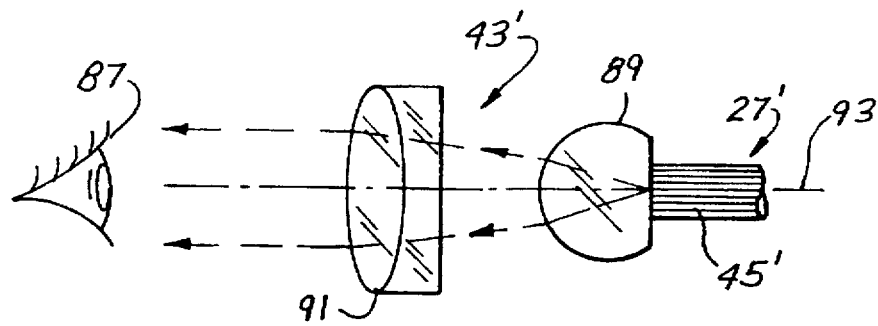
FIG. 12 is a schematic diagrammatic view of an embodiment illustrating an inventive feature which permits an endoscope to have a much greater depth of focus, and therefore greater tolerance of focusing effects.

FIG. 1 shows an endoscope 11 which generally comprises an endoscope body 13 and various optical components described below. The endoscope body 13 includes an elongated, tubular cylindrical sheath 15 and an eyepiece housing 17 attached to the sheath. Although the sheath 15 may be flexible or rigid, in this embodiment, the sheath 15 is rigid and is constructed of a rigid polymeric material or a suitable metal, such as stainless steel.

The sheath 15 is attached to the eyepiece housing 17 in any suitable conventional manner. Although the features of this invention are applicable to endoscopes for industrial uses, in the illustrated embodiment of the invention, the endoscope is adapted for medical use such as laparoscopy or arthroscopy.

The endoscope 11 includes illumination optics in the form of illumination optical fibers 19 (FIGS. 2 and 3) which extend from a distal end 21 of the endoscope body 13 through the sheath and a light cable connector 23 of the eyepiece housing 17. The connector 23 is adapted to be coupled to a source of illumination (not shown) so that light can be transmitted by the optical fibers 19 to the distal end 21 of the endoscope body 13 to illuminate the field of view.

The optical components also include an objective or distal lens 25 (FIGS. 2 and 3) which has a distal end 26 and which is carried by the endoscope body 13 adjacent the distal end 21 and an elongated fiberoptic image guide 27 in the endoscope body for transmitting an image proximally. The image guide 27 extends completely through the sheath 15 and terminates in the eyepiece housing 17 (FIG. 4).

The image guide 27 comprises a rigid, fused bundle of optical fibers 29 which are shown somewhat schematically in FIG. 3. Each of the fibers 29 is capable of transmitting or relaying a portion or pixel of an image such that the combined output of the image guide is an image.

An index matching medium in the form of an index matching adhesive or optical adhesive 31 is employed at an interface 33 between the distal lens 25 and the image guide 27 to adhere the distal lens to the image guide. To further mount these two components, a bushing 35 having a passage 37 receives the distal lens 25 and the distal end portion 38 of the image guide 27. The distal lens 25 and the distal portion of the image guide 27 are coupled to the bushing by a suitable adhesive. Also, the bushing 35 is coupled or secured to the sheath 15 by a suitable adhesive, so that the distal end portion 38 of the image guide is secured to the sheath.

Although various different orientations may be employed, such as a coaxial arrangement, in the illustrated embodiment the bushing 35 is located adjacent the sheath 15 (FIG. 2) and the illumination optical fibers 19 are arranged around the bushing. An adhesive, such as epoxy 39, joins the illumination optical fibers 19 together at the distal ends of the fibers.

The image formed at the image plane of the objective lens along the interface 33 is transmitted by the image guide 27 proximally to a proximal end surface 41 (FIG. 4) of the image guide. In the embodiment shown in FIG. 4, ocular lens 43 is carried by the eyepiece housing 17. The proximal end portion 45 of image guide 27 passes through a passage 47 defined in a slider element or positioning assembly 49. Proximal end portion 45 is secured to the slider element 49, for example, by a suitable adhesive. Slider element 49 is free to move axially in the space 51 defined by the cylindrical sidewall 53 of eyepiece housing 17. Thus, the proximal end portion 45 of image guide 27 is not secured or affixed to eyepiece housing 17 (or endoscope body 13 in general) and is free to move axially relative to the eyepiece housing.

The cross-section of the slider element 49 is substantially equal to the cross-section of space 51, but is sufficiently smaller that an adequate clearance is created between the outer surface of the slider element and the inner surface of the eyepiece housing to permit the free axial movement of the slider element in the space. In addition, passage 47 is substantially co-axial with the longitudinal axis 55 of the image guide 27. Thus, slider element 49, although being free to move axially within space 51, acts to maintain the positioning of the proximal end portion 45 of image guide 27 substantially coaxially with the longitudinal axis 55 of the image guide 27. Slider element 49 is effective to maintain the radial positioning of the proximal end surface 41 and proximal end portion 45 of image guide 27 relative to optical lens 43 to reduce any lateral optical displacement that may occur because the proximal end portion 45 is free to move axially relative to eyepiece body 17.

Having the proximal end portion 45 of image guide 27 axially moveable relative to endoscope body 13 provides substantial advantages. This feature allows one to expose endoscope 11 to widely varying temperatures without damaging the mechanical or optical integrity of the endoscope. Thus, for example, medical endoscope 11 can be sterilized at elevated temperatures (such as about 150° F. to about 250° F. or more) between uses to avoid cross-patient microbial contamination without damaging the endoscope, even though the image guide 27 and sheath 15 are made of materials having widely varying coefficients of thermal expansion. Even in non-medical applications, the endoscope can be used at widely varying temperatures without damage. Moreover, the use of slider element 49 effectively maintains the radial positioning of the proximal end face 41 relative to the endoscope body 13 to reduce the lateral optical displacement which may result from axially moving the proximal end portion 45.

The proximal end surface 41 of the image guide 27 forms an object plane for the ocular lens 43 and the ocular lens 43 transmits an image of the object at the object plane proximally to an eye cup 57 for direct viewing by the user of the endoscope 11. Alternatively, the ocular lens 43 may direct the image of the object to a suitable camera for enabling the image to be viewed on a TV monitor.

Another method for allowing non-constrained axial motion would be to substantially secure the proximal portion of the image guide with an elastomeric sealing member. Such a member could be formed or cured in place using room temperature vulcanizing silicone or the like. Once cured, this material would be adhered to the proximal portion of the image guide and the proximal housing of the endoscope body. Due to the elastomeric nature of the silicone material, axial shifts between the image guide and endoscope body would be compensated for by the compliance of the material. In motion, the elastomeric material would behave like a diaphragm, as long as adequate space were provided for displacement and flexing of the material.

In such an alternative construction, with reference to FIG. 4, the positioning assembly 49 would be constructed from an elastomeric sealing member and an interface of adherence or bonding would be created on the passage 47. Likewise, there would be a bond created between the positioning assembly 49 and the peripheral sidewall 53. Then, as the proximal end portion 45 of the image guide were axially displaced from the endoscope body and the proximal eyepiece housing 17, due to thermal effects or mechanical tolerancing, the interface bond at the passage 47 would be maintained.

FIGS. 6 and 7 illustrate an alternate endoscope, shown generally at 111, which is structured and functions similarly to endoscope 11 except as expressly stated herein. Components of endoscope 111 which correspond to components of endoscope 11 are given the same reference numeral, preceded by a 1.

The primary difference between endoscope 111 and endoscope 11 is in the structure at the proximal end portion of the endoscope. Eyepiece housing 117 includes an inwardly extending circumferential projection 61 which defines a centrally located passage 63 which is co-axial with longitudinal axis 155. Passage 63 has a slightly larger radial cross-sectional area than does fiberoptic image guide 127 so that the proximal end portion 145 of the image guide is free to move axially in the passage. However, the size and positioning of passage 63 are such as to substantially maintain the radial positioning of proximal end surface 141 and proximal end portion 145 relative to eyepiece homing 117 as the proximal end portion moves axially in the passage. Proximal end portion 145 is not secured to projection 61. Projection 61 is formed, for example, by conventional molding techniques, to be integral with the eyepiece housing 117. Of course, if desired, a separate element could be used and secured to the inner wall of the eyepiece housing to comprise the projection 61. The housing 117 could then be structured substantially similar to eyepiece housing 17.

FIGS. 8 and 9 illustrate another alternative endoscope, shown generally at 211, which is structured and functions similarly to endoscope 11, except as expressly stated herein. Components of endoscope 211 which correspond to components of endoscope 11 are given the same reference numeral preceded by a 2.

The primary difference between endoscope 211 and endoscope 11 is in the structure at the proximal end portion of the endoscope. Eyepiece housing 217 includes an inwardly extending circumferential projection 67 which defines a centrally located passage 69 which is coaxial with longitudinal axis 255. Passage 69 has a substantially larger radial cross-sectional area than does fiberoptic image guide 227. Projection 67 includes two annular grooves 71 and 73. Annular resilient O-rings 75 and 77 am captured in grooves 71 and 73, respectively. The grooves and O-rings are sized and positioned so that the O-rings come into contact with or receive the proximal end portion 245 of fiberoptic image guide 227. However, the proximal end-portion 245 is not secured to either the projection 67 or the O-rings 75 and 77 so that the proximal end portion of the image guide is free to move axially in the passage 69. The size and positioning of passage 69, grooves 71 and 73 and O-rings 75 and 77 are such as to substantially maintain the radial position of proximal end surface 241 and proximal end portion 245 relative to eyepiece housing 217 as the proximal end portion moves axially in the passage. Projection 67, including grooves 71 and 73, is formed, for example, by conventional molding techniques, to be integral with the eyepiece housing 217. Of course, if desired, a separate element in the form of projection 67 with grooves 71 and 73 can be used and secured to the inner wall of the eyepiece housing, which could be structured substantially similar to eyepiece housing 17.

FIGS. 10 and 11 illustrate a further endoscope, shown generally at 311, which is structured and functions similarly to endoscope 11, except as expressly stated herein. Components of endoscope 311 which correspond to components of endoscope 11 are given the same reference numeral preceded by a 3.

The primary difference between endoscope 311 d endoscope 11 is in the structure at the proximal end portion of the endoscope. Eyepiece housing 317 defines an interior space 79 in which is located a slider element 81. Proximal end portion 345 of fiberoptic image guide 327 is secured to slider element 81 and extends into an axially extending passage defined by the slider element. This axially extending passage is co-axial with longitudinal axis 355 of endoscope 311. Slider element 81 includes an annular groove 83 into which is placed an O-ring seal 85. In this embodiment, ocular lens 343 is carried by slider element 81.

Slider element 81 is free to move axially in the space 79. Thus, the proximal end portion 345 of image guide 327 is not secured to eyepiece housing 317 and is tee to move axially relative to the eyepiece housing. This axial movement also results in the axial movement of the slider element 81 and the ocular lens 343. Since there is substantially no relative movement between the ocular lens 343 and the proximal end face 341 of fiberoptic image guide 327, the defocusing effects caused by the axial movement of the proximal end portion 345 are reduced.

The cross-section of slider element 81, other than at the area of the groove 83, is substantially equal to the cross-section of space 79, but is sufficiently smaller that an adequate clearance is created between the outer surface of the slider element and the inner surface of the eyepiece housing to permit the free axial movement of the slider element in the space. Slider element 81, although being free to move axially within space 79, acts to maintain the positioning of the proximal end portion 345 of image guide 327 substantially co-axially with the longitudinal axis 355 of endoscope 311. The O-ring seal 85 is sized and adapted to come into contact with the interior side wall 87 of eyepiece housing 317. Thus, as slider element 81 moves axially within space 79, the O-ring seal 85 is effective to prevent fluid from passing thereacross.

FIG. 12 illustrates yet another important feature of the invention, which is applicable to any of the embodiments of FIGS. 4, 6, 8, or 10, as well as to the embodiments of FIGS. 13 and 14, to be described hereinbelow. Those elements corresponding to equivalent elements in the FIG. 4 embodiment are designated by the same reference numeral, primed.

As described in the Background of the Invention portion of the specification, a significant problem in endoscopes of the type described, particularly when the proximal end portion 45' of the fiberoptic image guide 27' is permitted to move axially with respect to the ocular lens, as is the case in all of the FIG. 4, 6, 8, and 10 embodiments, is that the depth of focus of the ocular lens system is very shallow. Thus, in conditions with varying thermal environments, or using an endoscope with high flexural properties, the image guide may undergo axial displacement relative to the endoscope body, resulting in the image quickly becoming out of focus as the proximal end portion 45' moves axially. Consequently, frequent focus adjustments are required, thereby impeding the procedure for which the endoscope is being used. Furthermore, such a shallow depth of focus renders the use of a fixed focus eyepiece practically impossible. Therefore, an important concept of the invention is to split the relatively high magnifying power of the eyepiece by the use of an ocular lens assembly 43', which comprises both a decoupling lens unit 89 and an eye lens unit 91. For example, rather than using a single eyepiece having a magnification of 40x, an eye lens unit having a magnification of 4x and a decoupling lens unit having a magnification of 10x could be employed, since the total magnification of the ocular lens assembly 43' is equal to the magnification of the decoupling lens unit 89 multiplied by the magnification of the eye lens unit 91.

On the proximal end portion 45' of the fiberoptic image guide, the decoupling lens unit 89 is placed in a fixed mechanical relationship to the fiberoptic. The eye lens unit 91 is not in a fixed mechanical relationship with the decoupling lens unit 89, but rather is fixed to the proximal housing portion, or eyepiece housing (not shown in FIG. 12) of the endoscope. The decoupling lens unit 89 is chosen to have a relatively high magnifying power, representing a major portion of the power of the entire ocular lens assembly 43'. Because of the high power of this first lens unit, any axial movement of this unit with respect to the eye lens unit is significantly reduced in its effect on the focus of the system.

In the preferred embodiment, the fixed mechanical relationship between the decoupling lens unit and the proximal end portion of the fiberoptic image guide is created by placing the lens unit in direct optical contact with the proximal end of the fiberoptic. This can be accomplished, for example, with an index-matched adhesive system. In the FIG. 12 embodiment, a hyper-hemi-spherical lens 89 is cemented to the fiberoptic imaging bundle 27. It is preferably chosen to have the form of an aplanatic lens, whose magnification equals the square of its refractive index. Such a lens element is known to be free of spherical aberration and cog thereby greatly reducing the aberrations contributed by the lens. In one example, with a commonly used high-index, low dispersion glass such as SCHOTT LAFN21, the refractive index is 1.788 at a 587 nm wavelength, and therefore the lateral magnification of an aplanatic lens made with this type of glass is $1.788^2=3.20x$. It is well known that the longitudinal magnification (i.e. along the optical axis 93) is equal to the square of the lateral magnification, which in this case becomes:

$$\text{Longitudinal magnification} = \text{Lateral magnification}^2 = 3.20^2 = 10.22x \quad (1)$$

Therefore, placing the lens unit 89 in contact with the fiber bundle 27 reduces sensitivity to focusing, in this example, by about a factor of ten. In a typical case, the depth of focus for a fiber having a diameter of 5 microns and a numerical aperture of 0.50 is about ten microns (about 0.0004 inches). This focus tolerance is difficult to maintain economically. However, introduction of split optics in the ocular lens assembly 43', as in the FIG. 12 example, including the decoupling lens unit 89, which is in direct optical contact with the imaging bundle 27', would in the above example increase the focus tolerance to about 100 microns (0.0040 inches). This level of focus tolerance is relatively easy to achieve. Alternatively, the resultant easing of focus sensitivity may be used to accommodate the thermal expansion of the length of the fiber bundle, as is discussed above with respect to the previous embodiments, such as that shown in FIG. 4.

Many variations are possible in implementing the inventive concept of splitting the ocular lens assembly optics. For example, while it is preferred that the decoupling lens unit 89 be in direct optical contact with the fiberoptic image guide 27', it is not required. This configuration merely reduces reflection losses and simplifies lens mounting. All that is necessary is that the fiberoptic image guide and the decoupling lens unit be in a fixed mechanical relationship, so that they move in concert. Also, considerable departure from the aplanatic lens form can be used to give somewhat higher magnification in the decoupling lens unit and thus give even more focus desensitizing effect.

The remaining optics in the ocular lens assembly 43' can be more complex than as shown in FIG. 12. This might particularly be the case if the decoupling lens is not aplanatic. The additional lenses might be needed to compensate for the aberrations of the decoupling lens.

Figure 13:
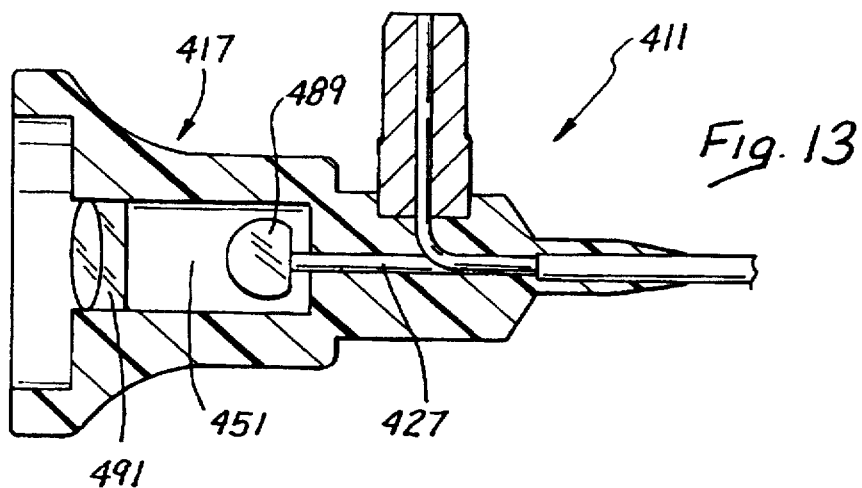
FIG. 13 is an axial sectional view through a proximal region of a fourth alternate endoscope constructed in accordance with the teachings of the present invention.

FIG. 13 illustrates yet another endoscope embodiment, shown generally at 411, which is structured and functions similarly to endoscope 11, except as expressly stated herein. Components of endoscope 411 which correspond to components of endoscope 11, or to components illustrated in FIG. 12, are given the same reference numeral preceded by a 4.

In FIG. 13, the proximal housing portion or eyepiece housing 417 of an endoscope 411 is shown, wherein the concept of split optics illustrated in FIG. 12 is embodied. Thus, the fiberoptic image guide 427 has at its proximal end a decoupling lens unit 489 affixed thereto, preferably using an index matched adhesive system. The decoupling lens unit 489 extends into the space 451, and is adapted to move axially in conjunction with the axial movement of the fiber bundle 427, due to thermal expansion or mechanical part tolerancing. Proximally of the decoupling lens unit 489 is an eye lens unit 491, which is fixedly attached in a known fashion, either adhesively or mechanically, to the proximal housing portion 517, as illustrated. This embodiment essentially operates like that shown diagrammatically in FIG. 12. Preferably, the lens unit 489 is aplanatic, being a hyper-hemi-spherical lens, and the eye lens unit 491 comprises a plurality of lenses, particularly an achromat, but almost any type of lens or lenses may be used to comprise either lens unit while remaining within the scope of the invention.

Figure 14:
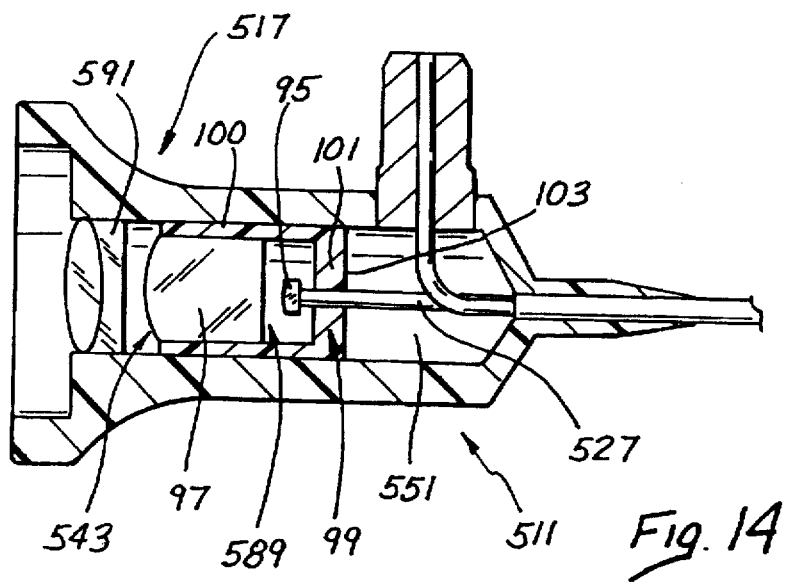
FIG. 14 is an axial sectional view through a proximal region of a fifth alternate endoscope constructed in accordance with the teachings of the present invention.

FIG. 14 illustrates a further alternative endoscope embodiment, shown generally at 511, which is structured and functions similarly to endoscope 11, except as expressly stated herein. Components of endoscope 511 which correspond to components of endoscope 11, or to components illustrated in FIG. 12, are given the same reference numeral preceded by a 5.

The endoscope 511 includes a further refinement of the concepts shown in FIGS. 12 and 13, wherein the ocular lens assembly 543 comprises a plurality of lenses in each of the decoupling lens unit 589 and the eye lens unit 591. As in the case of the FIG. 13 embodiment, the eye lens unit 591 preferably comprises a plurality of lenses, particularly an achromat. However, in this embodiment, the decoupling lens unit also comprises a plurality of lenses, preferably two as illustrated, though more could be utilized as well. A fast lens 95 is in direct optical contact with the proximal end of the fiberoptic image guide 527, preferably affixed thereto using an index-matched optical adhesive system, as in the FIGS. 12 and 13 embodiments. Again, however, direct optical contact is preferred, but only a fixed mechanical relationship is actually required. Proximally spaced from the first lens 95 is a second lens 97, which is fixedly attached to a decoupling lens unit cell 99. The second lens 97 is preferably fixedly attached to a peripheral wall portion 100 of the decoupling lens unit cell 99 using either an adhesive, such as an index-matched optical adhesive system, or mechanically, such as by a retaining ring or the like. The fiberoptic image guide 527 extends proximally through a base portion 101 of the decoupling lens unit cell 99, and is affixed thereto at a bond joint 103, preferably by means of an adhesive, though again a mechanical attachment means could be employed. The decoupling lens unit cell 99 essentially comprises a slider element, like that illustrated in FIGS. 4 and 10, for example, and is adapted to slide axially within the space 551, responsive to thermal expansion or mechanical part tolerancing. The cross-section of the decoupling lens unit cell 99 is substantially equal to the cross-section of the space 551, being just enough smaller so that a clearance is created which is sufficient to permit the axial sliding of the cell 99. An important function of the cell 99 is that it maintains the first and second lenses 95 and 97, respectively, in fixed axially spaced relationship to one another as they move axially with the cell through the space 551. As will be appreciated by one of ordinary skill in the art, further splitting the magnification power of the eye lens unit 591 between fast and second lenses 95 and 97, respectively, of the decoupling lens unit 589 is even more beneficial for improving the focus tolerance of the endoscope 511.

While this invention has been described with respect to various specific examples and embodiments, it is to be understood that the invention-is not limited thereto and that it can be variously practiced within the scope of the following claims.

What is claimed is:

1. An endoscope comprising:

an elongated endoscope body having a proximal housing portion;

an elongated fiberoptic image guide in said endoscope body, having a distal end and a proximal end, and being adapted for transmitting an image proximally through the endoscope, a proximal end portion of said fiberoptic image guide being disposed within said proximal housing portion; and an ocular lens assembly located in said proximal housing portion, including a decoupling lens unit and an axially spaced eye lens unit, wherein the decoupling lens unit is in direct fixed optical contact with the proximal end of the fiberoptic image guide, said decoupling lens unit being affixed to the proximal end of the fiberoptic image guide with an index-matched adhesive system;

wherein the proximal end portion of the fiberoptic image guide is axially movable relative to the proximal housing portion.

2. The endoscope of claim 1, wherein said decoupling lens unit has a higher magnifying power than said eye lens unit.

3. The endoscope of claim 1, wherein said eye lens unit is fixed to the endoscope proximal housing.

4. The endoscope of claim 1, wherein said decoupling lens unit comprises a hyper-hemi-spherical lens.

5. The endoscope of claim 1, wherein said decoupling lens unit comprises a plurality of lenses.

6. The endoscope of claim 5, wherein said plurality of lenses includes a first lens adjacent to the proximal end of said fiberoptic image guide and a second lens axially spaced from said first lens, between said first lens and said eye lens unit.

7. The endoscope of claim 6, wherein said first lens is in direct fixed optical contact with the proximal end of the fiberoptic image guide.

8. The endoscope of claim 7, wherein said first lens is affixed to the proximal end of the fiberoptic image guide with an index-matched adhesive system.

9. The endoscope of claim 5, wherein said decoupling lens unit includes a decoupling lens cell, having a base portion which is fixedly attached to the proximal end of the fiberoptic image guide and a peripheral wall portion which extends proximally toward said eye lens unit, said second lens being fixedly attached to said peripheral wall portion and said first lens being in direct fixed optical contact with the proximal end of the fiberoptic image guide, whereby said first and second lenses are in fixed axially spaced relationship to one another.

10. The endoscope of claim 9, wherein said decoupling lens cell is sized and adapted to move axially within said endoscope proximal housing portion, thereby varying the axial distance between said decoupling lens unit and said eye lens unit.

11. The endoscope of claim 1, wherein said eye lens unit comprises a plurality of lenses.

12. An endoscope comprising:
an endoscope body which is elongated and has a distal end and a proximal housing portion;
an elongated fiberoptic image guide in said endoscope body which is adapted for transmitting an image proximally through the endoscope, said fiberoptic image guide including a distal end portion which is secured to said endoscope body and a proximal end portion which is disposed within said proximal housing portion and is permitted to move axially relative to said proximal housing portion; and
an ocular lens assembly located in aid proximal housing portion, through which the image transmitted proximally by said fiberoptic image guide may be visualized, the ocular lens assembly including a decoupling lens unit and an axially spaced eye lens unit, wherein the decoupling lens unit is in a fixed mechanical relationship with the fiberoptic image guide and has a higher magnifying power than said eye lens unit, said eye lens unit being fixed to the endoscope proximal housing portion.

13. The endoscope of claim 12, wherein said endoscope body and said fiberoptic image guide are substantially rigid and the proximal end portion of the fiberoptic image guide is not secured to said endoscope body, said endoscope further comprising:
a distal lens assembly secured to said endoscope body and located distally of said fiberoptic image guide; and
a positioning assembly located in said endoscope body for substantially maintaining the radial position of said proximal end portion of said fiberoptic image guide relative to said endoscope body as said proximal end portion moves axially relative to said endoscope body.

14. The endoscope of claim 13, wherein said endoscope further comprises illumination optics carried by the endoscope body for transmitting illumination distally in said endoscope body.

15. The endoscope of claim 13, wherein said proximal end portion of said fiberoptic image guide is secured to said positioning assembly, which is adapted to move axially relative to said endoscope body.

16. The endoscope of claim 13, wherein said positioning assembly is operatively coupled to said endoscope body so as to be substantially stationary in the axial direction relative to said endoscope body.

17. The endoscope of claim 13, wherein said positioning assembly defines an axially extending passage in which said proximal end portion of said fiberoptic image guide is received, said positioning assembly being sized and adapted to move gaily relative to said endoscope body.

18. The endoscope of claim 13, wherein said positioning assembly includes a circumferential projection extending radially inwardly from said endoscope body and about said proximal end portion of said fiberoptic image guide, said circumferential projection being integral with said proximal housing portion.

19. The endoscope of claim 13, wherein said positioning assembly includes at least one resilient annular o-ring adapted to receive said proximal end portion of said fiberoptic image guide.

20. The endoscope of claim 13, wherein said positioning assembly carries the decoupling lens unit, said proximal end portion of said fiberoptic image guide being secured to said positioning assembly which, in turn, is sized and adapted to move axially relative to said endoscope body, said endoscope further comprising a seal assembly located between said endoscope body and said positioning assembly for effectively preventing the flow of fluid thereacross.

21. The endoscope of claim 12, wherein said endoscope body has a different coefficient of thermal expansion than said fiberoptic image guide.

22. The endoscope of claim 12, wherein the decoupling lens unit is in direct fixed optical contact with the proximal end of the fiberoptic image guide.

23. The endoscope of claim 12, wherein said decoupling lens unit comprises a hyper-hemi-spherical lens.

24. The endoscope of claim 12, wherein said decoupling lens unit includes a lens in direct fixed optical contact with the proximal end of said fiberoptic image guide, said lens having optical magnification power, and said eye lens unit comprising a plurality of lenses.

25. An endoscope comprising:
an elongated endoscope body having a proximal housing portion;
an elongated fiberoptic image guide in said endoscope body, having a distal end and a proximal end, and being adapted for transmitting an image proximally through the endoscope, a proximal end portion of said fiberoptic image guide being disposed within said proximal housing portion; and
an ocular lens assembly located in said proximal housing portion, including a decoupling lens unit and an axially spaced eye lens unit, wherein the decoupling lens unit is in a fixed mechanical relationship with the proximal end of the fiberoptic image guide and includes a plurality of lenses, said plurality of lenses including a first lens in direct fixed optical contact with the proximal end of the fiberoptic image guide, and a second lens axially spaced from said first lens, between said first lens and said eye lens unit, the first lens being affixed to the proximal end of the fiberoptic image guide with an index-matched adhesive system;

wherein the proximal end portion of the fiberoptic image guide is axially movable relative to the proximal housing portion.

26. An endoscope comprising:

an elongated endoscope body having a proximal housing portion;

an elongated fiberoptic image guide in said endoscope body, having a distal end and a proximal end, and being adapted for transmitting an image proximally through the endoscope, a proximal end portion of said fiberoptic image guide being disposed within said proximal housing portion; and an ocular lens assembly located in said proximal housing portion, including a decoupling lens unit and an axially spaced eye lens unit, wherein the decoupling lens unit is in a fixed mechanical relationship with the proximal end of the fiberoptic image guide;

the decoupling lens unit comprising a plurality of lenses, including a first lens adjacent to the proximal end of said fiberoptic image guide and a second lens axially spaced from said first lens, between said first lens and said eye lens unit, the decoupling lens unit further including a decoupling lens cell, having a base portion which is fixedly attached to the proximal end of the fiberoptic image guide and a peripheral wall portion which extends proximally toward said eye lens unit, said second lens being fixedly attached to said peripheral wall portion and said first lens being adjacent to the proximal end of the fiberoptic image guide, whereby said first and second lenses are in fixed axially spaced relationship to one another, the decoupling lens cell being sized and adapted to move axially within said endoscope proximal housing portion, thereby varying the axial distance between said decoupling lens unit and said eye lens unit;

wherein the proximal end portion of the fiberoptic image guide is axially movable relative to the proximal housing portion.

27. An endoscope comprising:

an endoscope body which is elongated and has a distal end and a proximal housing portion;

an elongated fiberoptic image guide in said endoscope body which is adapted for transmitting an image proximally through the endoscope, said fiberoptic image guide including a distal end portion which is secured to said endoscope body and a proximal end portion which is disposed within said proximal housing portion and is permitted to move axially relative to said proximal housing portion;

an ocular lens assembly located in said proximal housing portion, through which the image transmitted proximally by said fiberoptic image guide may be visualized, the ocular lens assembly including a decoupling lens unit and an axially spaced eye lens unit, wherein the decoupling lens unit is in a fixed mechanical relationship with the fiberoptic image guide;

the decoupling lens unit including a decoupling lens cell, having a base portion which is adjacent to the proximal end of the fiberoptic image guide and a peripheral wall portion which extends proximally toward said eye lens unit, a plurality of lenses disposed in said decoupling lens cell, including a first lens adjacent to the proximal end of said fiberoptic image guide and a second lens axially spaced from said first lens, said second lens being fixedly attached to said peripheral wall portion by means of an index-matched adhesive system, whereby said first and second lenses are in fixed axially spaced relationship to one another, said decoupling lens unit comprising a slider element and being sized and adapted to slide axially within said endoscope proximal housing portion, thereby varying the axial distance between said decoupling lens unit and said eye lens unit.

28. The endoscope of claim 27, wherein said base portion is fixedly attached to the proximal end of the fiberoptic image guide.

29. The endoscope of claim 27, wherein said first lens is in direct fixed optical contact with the proximal end of the fiberoptic image guide.

30. An endoscope comprising:

an elongated endoscope body having a proximal housing portion;

an elongated fiberoptic image guide in said endoscope body, having a distal end and a proximal end, and being adapted for transmitting an image proximally through the endoscope, a proximal end portion of said fiberoptic image guide being disposed within said proximal housing portion; and an ocular lens assembly located in said proximal housing portion, including a decoupling lens unit and an axially spaced eye lens unit, wherein the decoupling lens unit is in a fixed mechanical relationship with the proximal end of the fiberoptic image guide and the eye lens unit is fixed to the endoscope proximal housing;

wherein the proximal end portion of the fiberoptic image guide is axially movable relative to the proximal housing portion.

* * * * *